United States Patent [19]
Fujimura et al.

[11] 3,994,890
[45] Nov. 30, 1976

[54] 1-AMINOALKYL, 3-PHENYL INDAZOLES

[75] Inventors: Yasuo Fujimura, Tokyo; Hiroyuki Nagano, Ageo; Minoru Shindo, Kurume; Morio Kakimoto, Kawagoe; Tsuneo Iwasaki, Ageo; Yugo Ikeda, Hoya, all of Japan

[73] Assignee: Chugai Seiyaku Kabushiki Kaisha, Tokyo, Japan

[22] Filed: Jan. 15, 1975

[21] Appl. No.: 541,100

[30] Foreign Application Priority Data
Jan. 31, 1974 Japan............... 49-12184
May 18, 1974 Japan............... 49-55000
June 3, 1974 Japan............... 49-61853
Nov. 12, 1974 Japan............... 49-129521
Nov. 26, 1974 Japan............... 49-135184

[52] U.S. Cl.................. 260/247.5 EP; 260/268 BC; 260/293.6; 260/296 B; 260/310 C; 424/248; 424/250; 424/263; 424/267; 424/273

[51] Int. Cl.²........................................ C07D 413/06

[58] Field of Search............. 260/247.5, 268, 293.6, 260/296, 310, 247.5 EP, 268 BC, 296 B, 310 C

[56] References Cited
UNITED STATES PATENTS

| | | | |
|---|---|---|---|
| 3,641,050 | 2/1972 | Minieri............... | 260/310 C |
| 3,736,332 | 5/1973 | Butula............... | 260/310 C |
| 3,763,180 | 10/1973 | Sauli............... | 260/310 C |
| 3,766,192 | 10/1973 | Minieri............... | 260/310 C |

*Primary Examiner*—Henry R. Jiles
*Assistant Examiner*—R. W. Ramsuer
*Attorney, Agent, or Firm*—Browdy and Neimark

[57] ABSTRACT

Indazole derivatives represented by the formula

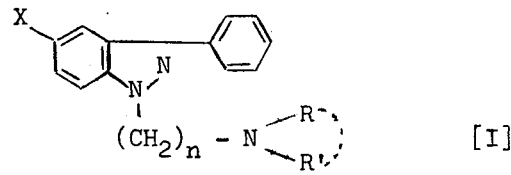

wherein X is hydrogen, halogen atom or lower alkyl group; R and R' each is hydrogen, lower alkyl group or lower alkenyl group and when taken together with the nitrogen atom to which they are attached form an unsubstituted or substituted heterocyclic ring; and n is an integer of 1 – 3 are novel compounds having tranquilizing activity, antidepressive activity, anti-inflammatory activity, circulatory activity etc. and are useful as medicines.

34 Claims, No Drawings

1-AMINOALKYL, 3-PHENYL INDAZOLES

The invention relates to indazole derivatives represented by the formula:

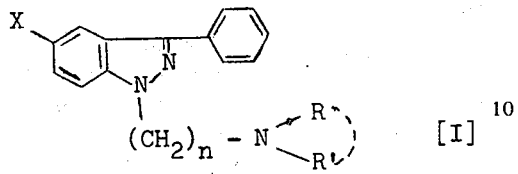  [I]

wherein X is hydrogen, halogen atom or lower alkyl group; R and R' each is hydrogen, lower alkyl group or lower alkenyl group and when taken together with the nitrogen atom to which they are attached form an unsubstituted or substituted heterocyclic ring; and n is an integer of 1 – 3.

The indazole derivatives represented by the formula [I] are novel compounds having tranquilizing activity, antidepressive activity, anti-inflammatory activity, circulatory activity etc. and are useful as medicines.

According to the invention compounds represented by the formula [I] are prepared as follows:

1. a compound of the invention wherein neither $R_1$ nor $R_2$ is hydrogen is prepared by the reaction of a compound represented by the formula:

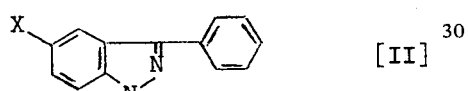  [II]

wherein X is as defined above with a compound represented by the formula:

  [III]

wherein X' is halogen atom; $R_1$ and $R_2$ each is lower alkyl group or lower alkenyl group and when taken together with the nitrogen atom to which they are attached form an unsubstituted or substituted heterocyclic ring; n is as defined above.

2. a compound represented by the formula [I] wherein n is 2 or 3 is prepared by reducing a compound represented by the formula:

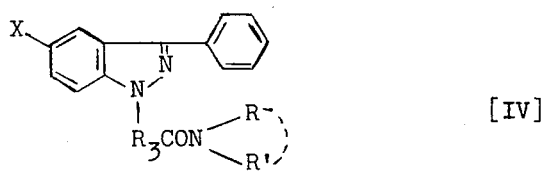  [IV]

wherein $R_3$ is methylene or ethylene group; X, R and R' are as defined above.

3. a compound represented by the formula [I] wherein n is 1 is preparing by the reaction of a compound represented by the formula:

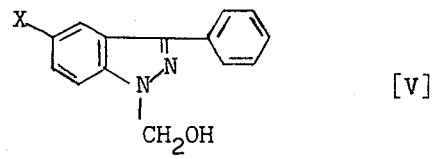  [V]

wherein X is as defined above with an amine represented by the formula:

  [VI]

wherein R and R' are as defined above.

4. A compound represented by the formula [I] wherein both R and R' are hydrogen is prepared by the reaction of a compound represented by the formula:

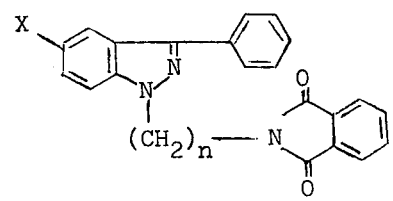  [VII]

wherein X and n are as defined above with hydrazine.

In the formulae [I], [IV] and [VI] R and R' may be the same or different and R and R' taken together may form a heterocyclic ring which may be substituted by a methyl group, phenyl group, etc. In the definition of R and R' lower alkyl group is of from 1 to 4 carbon atoms and exemplified by methyl group, ethyl group, n-butyl group, etc. And lower alkenyl group is of from 2 to 4 carbon atoms, for example, allyl group. Heterocyclic ring is exemplified by morpholino group, piperidino group, piperazino group, pyrrolidino group, 1,2,3,6-tetrahydropyridino group, phthalimido group, etc.

The compound of the formula [II] used in the process (1) as a starting material can be obtained by diazonizing a 2-aminobenzophenone derivative, ring-closing the diazonized product with sodium sulfite and treating the product with stannous chloride (Berichte der Deutschen Chemischen Gesellschaft, vol. 29, p. 1255 (1896)).

The compound of the formula [IV] used in the process (2) as a starting compound is a novel compound and is prepared by, for example, the following reaction:

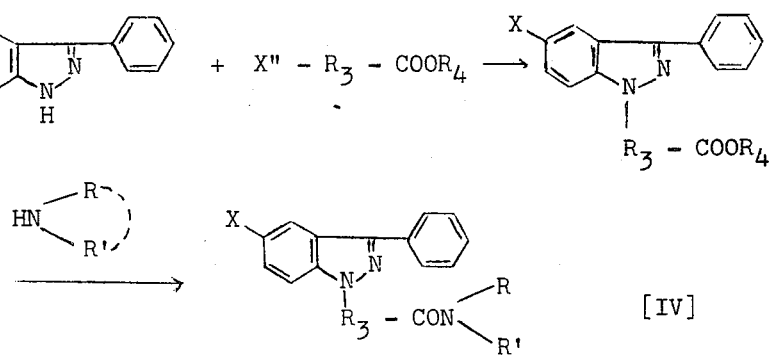

wherein X, R, R' and $R_3$ are as defined above; X'' is halogen atom; and $R_4$ is lower alkyl group.

The compound of the formula [V] used in the process (3) as a starting compound is prepared by reacting the compound of the formula [II] with formaldehyde and industrially without separation of this intermediate it can be immediately reacted with the amine of the formula [VI].

In the practice of the process (1) of the invention the reaction of the compound of the formula [II] with the compound of the formula [III] is carried out in a suitable organic solvent, for example dimethylformamide, toluene, methanol, ethanol etc. and at a temperature of room temperature or above generally for 10 – 90 minutes.

It is preferable to use an excessive molar amount of the compound of the formula [III] in comparison with the compound of the formula [II]. And in order to carry out the reaction smoothly and increase the yield, it is favorable to use a condensating agent, for example, an equimolar amount or an excessive molar amount of sodium hydride, sodium alcoholate, sodium amide or sodium hydroxide. In the case wherein the starting compound of the formula [III] is in the form of hydrochloric acid salt, it is used after the conversion to a free amine with the use of base such as sodium hydroxide and dissolving the free amine in a solvent such as toluene.

And in the industrial practice of this process, if a quarternary ammonium salt such as triethylbenzylammonium chloride is used as a phase transfer catalysis, water can be used as a solvent.

In the practice of the process (2), the reduction reaction of the compound of the formula [II] is carried out at a temperature of room temperature or above; preferably reflux temperature of the reaction mixture, for 10 – 60 minutes after dissolving the compound (II) in a suitable solvent such as tetrahydrofuran, diethyl ether etc. and adding an equimolar or excessive molar amount of a usual reducing agent such as lithium aluminum hydride etc. to the solution.

In the practice of the process (3), the compound of the formula [V] is reacted with the amine of the formula [VI] in a suitable solvent, for example ethanol, methanol etc. The reaction is carried out at room temperature or a temperature higher than room temperature, preferably reflux temperature of the reaction mixture, for 1 – 5 hours. Preferably the amine of the formula [VI] is used in the equimolar or an excessive molar amount in comparison with the amount of the compound of the formula [V]. An appropriate catalyst such as sodium hydroxide, potassium hydroxide etc. may be used. When the object compound is obtained from the compound of the formula [II] through the compound of the formula [V], the reaction can be carried out in a one-step procedure by adding formaldehyde and amine simultaneously to the compound of the formula [II] and reacting them under similar conditions.

In the practice of the process (4), the compound of the formula [VII] is dissolved in an organic solvent such as ethanol and reacted with an equimolar or excessive molar amount of hydrazine, preferably hydrazine hydrate. The reaction is carried out at room temperature or a temperature above it, preferably reflux point of the solvent for 1 – 4 hours.

Isolation of the object product [I] from the reaction mixture is carried out by pouring the reaction mixture into ice-water, extracting the mixture with an organic solvent such as benzene, chloroform etc., washing the extract with water, drying the extract and further concentrating it. The object product [I] is generally an oil and can be converted to an inorganic acid salt thereof such as hydrochloride and sulfate or an organic acid salt such as oxalate, malonate and succinate.

The compound of the formula [I] obtained according to the invention is a novel compound and is useful as a medicine having tranquilizing activity, antidepressive activity, anti-inflammatory activity, circulatory activity, etc.

The following examples are intended only to explain the invention in detail and the invention is not limited by the examples.

EXPERIMENTAL EXAMPLE 1

Anti-reserpine activity ddY Strain male mice (4 – 5 weeks old, body weight 23 – 25 g) were intraperitoneally treated with 5 mg/kg of reserpine and after 3 hours the rectal temperatures were determined. Referring to the determined temperatures, the mice were divided into groups of 6 mice each to make the mean temperature of each group as much the same as possible. 4 hours after the administration of reserpine, 100 mg/kg each of the samples was orally administered to the mice. Rectal temperatures were determined 1 hour and 3 hours after the oral administration of the samples and effects of the samples on rectal temperature were calculated as a ratio with the control drug, that is, imipramine, according to the following equation to obtain the values shown in Table 1.

$$T = \frac{\text{Temperature difference between groups treated with samples and a control group (treated with vehicle)}}{\text{Temperature difference between a group treated with imipramine and a control group (treated with vehicle)}}$$

Table 1

| Samples | Anti-reserpine activity |
| --- | --- |
| Compound of Example 3 | 0.7 |
| Compound of Example 7 | 1.0 |
| Compound of Example 8 | 0.7 |
| Compound of Example 9 | 0.7 |
| Compound of Example 10 | 1.0 |
| Compound of Example 16 | 0.5 |
| Compound of Example 29 | 1.0 |
| imipramine | 1.0 |
| desipramine | 1.0 |

EXPERIMENTAL EXAMPLE 2

Barbiturate potentiation ddY Strain male mice (4 – 5 weeks old, body weight 23 – 28 g) in groups of 5 mice each were orally treated with 100 mg/kg of samples and 30 minutes after the oral administration the mice were intraperitoneally treated with 100 mg/kg of hexobarbital. Duration of loss of righting reflex due to hexobarbital was determined and barbiturate potentiation ratios with control groups were calculated. The calculated values are given in Table 2. Imipramine, desipramine and diazepam were used as control drugs.

Table 2

| Samples | Barbiturate potentiation |
| --- | --- |
| Compound of Example 1 | 3.0 |
| Compound of Example 2 | 1.5 |
| Compound of Example 3 | 1.5 |
| Compound of Example 4 | 1.2 |
| Compound of Example 6 | 2.9 |
| Compound of Example 7 | 1.9 |
| Compound of Example 8 | 1.3 |
| Compound of Example 10 | 1.0 |
| Compound of Example 11 | 1.3 |
| Compound of Example 12 | 1.0 |
| Compound of Example 14 | 1.7 |
| Compound of Example 15 | 1.4 |
| Compound of Example 17 | 1.0 |
| Compound of Example 19 | 1.2 |
| Compound of Example 20 | 1.6 |
| Compound of Example 23 | 1.3 |
| Compound of Example 25 | 1.1 |
| Compound of Example 29 | 1.7 |
| Compound of Example 34 | 2.5 |
| imipramine | 1.3 |
| desipramine | 1.5 |
| diazepam* | 2.3 |

*5 mg/kg was orally administered.

EXPERIMENTAL EXAMPLE 3 ddY Strain mice and Wistar-Imamichi strain rats were used to inspect acute toxicity and subacute toxicity (30 days; oral administration) of a compound of the formula [I].

Table 3

| Sample | Animal | $LD_{50}$ (mg/kg p.o.) | | Subacute toxicity |
| --- | --- | --- | --- | --- |
| | | mouse | rat | rat |
| Compound of Example 10 | | 580 | 3000~ | not fatal at a dose of 100 mg/kg; no abnormal symptom at this dose. |
| | | 660 | 5000 | |
| Imipramine | | 350 | 900 | not fatal at a dose of 50 mg/kg; At this dose normal increase in body weight is depressed and hemoglobin and blood urine nitrogen are reduced. Marginal part of liver appears dull. |

EXAMPLE 1

Dimethylaminoethyl chloride hydrochloride (4.32 g) was dissolved in water (20 ml) and the solution was alkalized by the addition of aqueous sodium hydroxide solution. Then the solution was thoroughly mixed with toluene (30 ml) and the organic layer was dried over sodium sulfate. Separately, 3-phenylindazole (3.88 g) was dissolved in dimethyl formamide (60 ml) and sodium hydride, 50% pure, (1.15 g) was added to the solution, followed by adding dropwise the previously prepared toluene solution. The mixture was heated to 70° C and stirred for 75 min. at that temperature and then poured into ice-water and extracted with chloroform. The extract was washed with water, dried over sodium sulfate and concentrated by evaporation. The residue was treated with ether-hydrochloric acid to form hydrochloride. The product was recrystallized from ethanol-ether to obtain 2.0 g of 1-dimethylaminoethyl-3-phenylindazole hydrochloride (m.p. 163°–165° C).

Analysis: Calcd. for $C_{17}H_{20}N_3Cl$: C, 67.65; H, 6.68; N, 13.92 (%) Found: C, 67.36; H, 6.59; N, 13.72 (%)

EXAMPLE 2

By the procedure similar to that described in Example 1, 3-phenyl-5-chloroindazole (4.57 g) and dimethylaminoethyl chloride hydrochloride (4.32 g) were treated to obtain 3.5 g of 1-dimethylaminoethyl-3-phenyl-5-chloroindazole hydrochloride (m.p. 200°–201° C).

Analysis: Calcd. for $C_{17}H_{19}N_3Cl_2$: C, 60.72; H, 5.70; N, 12.49 (%) Found: C, 60.99; H, 5.74; N, 12.53 (%)

EXAMPLE 3

By the procedure similar to that described in Example 1, 3-phenyl-5-methylindazole (4.17 g) and dimethylaminoethyl chloride hydrochloride (4.32 g) were treated to obtain 4.0 g of 1-dimethylaminoethyl-3-phenyl-5-methylindazole hydrochloride (m.p. 191°–192° C).

Analysis: Calcd. for $C_{18}H_{22}N_3Cl$: C, 68.45; H, 7.02; N, 13.30 (%) Found: C, 68.42; H, 7.17; N, 13.28 (%)

EXAMPLE 4

By the procedure similar to that described in Example 1, 3-phenyl-5-chloroindazole (4.57 g) and diethylaminoethyl chloride hydrochloride (5.16 g) were treated to obtain 5.1 g of 1-diethylaminoethyl-3-phenyl-5-chloroindazole hydrochloride (m.p. 185°–186° C).

Analysis: Calcd. for $C_{19}H_{23}N_3Cl_2$: C, 62.64; H, 6.36; N, 11.54 (%) Found: C, 62.41; H, 6.23; N, 11.33 (%)

EXAMPLE 5

By the procedure similar to that described in Example 1, 3-phenyl-5-methylindazole (4.17 g) and diethylaminoethyl chloride hydrochloride (5.16 g) were treated to obtain 4.0 g of 1-diethylaminoethyl-3-phenyl-5-methylindazole hydrochloride (m.p. 131°–133° C).

Analysis: Calcd. for $C_{20}H_{26}N_3Cl$: C, 69.85; H, 7.62; N, 12.22 (%) Found: C, 69.81; H, 7.59; N, 12.01 (%)

EXAMPLE 6

By the procedure similar to that described in Example 1, 3-phenylindazole (3.88 g) and diethylaminoethyl chloride hydrochloride (5.16 g) were treated to obtain 2.0 g of 1-diethylaminoethyl-3-phenylindazole hydrochloride (m.p. 114°–118° C).

Analysis: Calcd. for $C_{19}H_{24}N_3Cl.H_2O$: C, 65.60; H, 7.53; N, 12.08 (%) Found: C, 65.16; H, 7.25; N, 11.79 (%)

EXAMPLE 7

By the procedure similar to that described in Example 1, 3-phenylindazole (3.88 g) and dimethylaminopropyl chloride hydrochloride (4.74 g) to obtain 3.5 g of 1-dimethylaminopropyl-3-phenylindazole hydrochloride (m.p. 140°–143° C).

Analysis: Calcd. for $C_{18}H_{22}N_3Cl.2H_2O$: C, 61.44; H, 7.44; N, 11.94 (%) Found: C, 61.04; H, 7.55; N, 11.72 (%)

EXAMPLE 8

By the procedure similar to that described in Example 1, 3-phenyl-5-chloroindazole (4.57 g) and dimethylaminopropyl chloride hydrochloride (4.74 g) were treated to obtain 4.74 g of 1-dimethylaminopropyl-3-phenyl-5-chloroindazole hydrochloride (m.p. 158°–160° C).

Analysis: Calcd. for $C_{18}H_{21}N_3Cl_2$: C, 61.72; H, 6.04; N, 12.00 (%) Found: C, 61.47; H, 5.95; N, 11.71 (%)

EXAMPLE 9

By the procedure similar to that described in Example 1, 3-phenyl-5-bromoindazole (4.10 g) and dimethylaminopropyl chloride hydrochloride (3.56 g) were treated to obtain 4.0 g of 1-dimethylaminopropyl)-3-phenyl-5-bromoindazole hydrochloride (m.p. 149°–150° C).

Analysis: Calcd. for $C_{18}H_{21}N_3ClBr$: C, 54.77; H, 5.36; N, 10.65 (%) Found: C, 54.35; H, 5.46; N, 10.17 (%)

EXAMPLE 10

By the procedure similar to that described in Example 1, 3-phenyl-5-methylindazole (4.17 g) and dimethylaminopropyl chloride hydrochloride (4.74 g) were treated to obtain an oily product. The product was purified through distillation under reduced pressure to obtain 3.5 g of 1-dimethylaminopropyl-3-phenyl-5-methylindazole (b.p. 185°C/0.5 mmHg).

Analysis: Calcd. for $C_{19}H_{23}N_3$: C, 77.78; H, 7.90; N, 14.32 (%) Found: C, 77.68; H, 7.85; N, 14.11 (%)

The resulting oily product was reacted with oxalic acid to obtain 3.4 g of 1-dimethylaminopropyl-3-phenyl-5-methylindazole oxalate (m.p. 184°–185° C).

Analysis: Calcd. for $C_{21}H_{25}N_3O_4$: C, 65.78; H, 6.57; N, 10.96 (%) Found: C, 65.53; H, 6.58; N, 10.82 (%)

1-Dimethylaminopropyl-3-phenyl-5-methylindazole was converted by a conventional way to its hydrochloride having a melting point between 139°–140° C.

Analysis: Calcd. for $C_{19}H_{24}N_3Cl$: C, 69.18; H, 7.33; N, 12.74 (%) Found: C, 69.01; H, 7.28; N, 12.68 (%)

EXAMPLE 11

By the procedure similar to that described in Example 1, 3-phenylindazole (3.88 g) and piperidinopropyl chloride hydrochloride (5.94 g) were treated to obtain 5.3 g of 1-piperidinopropyl-3-phenylindazole hydrochloride (m.p. 201°–202° C).

Analysis: Calcd. for $C_{21}H_{26}N_3Cl$: C, 70.87; H, 7.36; N, 11.81 (%) Found: C, 71.11; H, 7.39; N, 11.89 (%)

EXAMPLE 12

By the procedure similar to that described in Example 1, 3-phenyl-5-methylindazole (4.17 g) and piperidinopropyl chloride hydrochloride were treated to obtain 5.0 g of 1-piperidinopropyl-3-phenyl-5-methylindazole hydrochloride (m.p. 222°–223° C).

Analysis: Calcd. for $C_{22}H_{28}N_3Cl$: C, 71.43; H, 7.63; N, 11.36 (%) Found: C, 71.50; H, 7.61; N, 11.47 (%)

EXAMPLE 13

3-Phenyl-5-methylindazole (4.17 g) was dissolved in dimethylformamide (70 ml) and sodium hydride 50% pure (1.15 g) was added to the solution, followed by stirring it at room temperature for 10 min. To the resulting solution was added dropwise a solution of diethylaminopropyl chloride (3.59 g) in 30 ml of toluene. The mixture was stirred at 70° C for 1 hour and poured into ice-water, and extracted with chloroform. The extract was washed with water, dried over sodium sulfate and concentrated by evaporation. The residue was treated with ether-hydrochloric acid to obtain 4.5 g of 1-diethylaminopropyl-3-phenyl-5-methylindazole hydrochloride (m.p. 127°–129° C).

Analysis: Calcd. for $C_{21}H_{28}N_3Cl$: C, 70.47; H, 7.89; N, 11.74 (%) Found: C, 70,24; H, 8.26; N, 11.28 (%)

EXAMPLE 14

By the procedure similar to that described in Example 13, 3-phenyl-5-chloroindazole (4.57 g) and morpholinoethyl chloride (3.59 g) were treated to obtain 3.7 jg of 1-morpholinoethyl-3-phenyl-5-chloroindazole hydrochloride (m.p. 226°–229° C).

Analysis: Calcd. for $C_{19}H_{21}N_3OCl_2$: C, 60.32; H, 5.60; N, 11.11 (%) Found: C, 60.55; H, 5.59; N, 11.22 (%)

EXAMPLE 15

By the procedure similar to that described in Example 13, 3-phenyl-5-methylindazole (4.17 g) and 1-morpholinopropyl chloride (3.93 g) were treated to obtain 4.1 g of 1-morpholinopropyl-3-phenyl-5-methylindazole hydrochloride (m.p. 180°–182° C).

Analysis: Calcd. for $C_{21}H_{26}N_3OCl$: C, 67.82; H, 7.05; N, 11.30 (%) Found: C, 67.89; H, 6.85; N, 11.36 (%)

EXAMPLE 16

By the procedure similar to that described in Example 13, 3-phenylindazole (3.88 g) and N-methylpiperazinopropyl chloride (4.24 g) were treated to obtain 6.8 g of 1-N-methylpiperazinopropyl-3-phenyl indazole hydrochloride (m.p. 222°–224° C).

Analysis: Calcd. for $C_{21}H_{28}N_4Cl_2.H_2O$: C, 59.29; H, 7.11; N, 13.17 (%) Found: C, 59.54; H, 7.02; N, 13.23 (%)

EXAMPLE 17

By the procedure similar to that described in Example 13, 3-phenyl-5-methylindazole (4.17 g) and N-methylpiperazinopropyl chloride (4.24 g) were treated to obtain 4.0 g of 1-N-methylpiperazinopropyl-3-phenyl-5-methylindazole hydrochloride (m.p. 226°–228° C).

Analysis: Calcd. for $C_{22}H_{30}N_4Cl_2.½ H_2O$: C, 61.39; H, 7.25; N, 13.02 (%) Found: C, 61.10; H, 7.01; N, 13.05 (%)

EXAMPLE 18

By the procedure similar to that described in Example 13, 3-phenyl-5-methylindazole (4.17 g) and diallylaminopropyl chloride (4.17 g) were treated to obtain 4.3 g of 1-diallylaminopropyl-3-phenyl-5-methylindazole hydrochloride (m.p. 81°–82° C).

Analysis: Calcd. for $C_{23}H_{28}N_3Cl$: C, 72.33; H, 7.39; N, 11.00 (%) Found: C, 72.74; H, 7.88; N, 11.07 (%)

EXAMPLE 19 a. 3-Phenyl-5-chloroindazole (2.29 g), paraformaldehyde (0.35 g), morpholine (1.91 g) and 1N aqeous sodium hydroxide solution (1 ml) were added to 40 ml of ethanol and the mixture was allowed to react under reflux. The reaction mixture was concentrated and then the residue was dissolved in chloroform, washed with water, dried over sodium sulfate and concentrated. The residue was treated with column chromatography to obtain 1.7 g of 1-morpholinomethyl-3-phenyl-5-chloroindazole having a melting point of between 155°–156° C after recrystallization from methanol.

Analysis: Calcd. for $C_{18}H_{18}N_3OCl$: C, 65.95; H, 5.53; N, 12.82 (%) Found: C, 65.63; H, 5.44; N, 12.69 (%)

b. 3-Phenyl-5-chloroindazole (9.16 g), paraformaldehyde (1.5 g), and 5% aqueous sodium hydroxide solution (1 ml) were added to ethanol (40 ml) and the mixture was heated under reflux for 3 hours. After cooling the mixture, the precipitated crystals were recovered by filtration to obtain 8.0 g of 1-hydroxmethyl-3-phenyl-5-chloroindazole (m.p. 144°–146° C).

Analysis: Calcd. for $C_{14}H_{11}N_2OCl$: C, 65.00; H, 4.29; N, 10.83 (%) Found: C, 65.21; H, 4.32; N, 10.71 (%)

The product obtained the above and paraformaldehyde were treated by the procedure similar to that described in (a) to obtain the same product as produced in (a).

EXAMPLE 20

By the procedure similar to that described in Example 19, 3-phenyl-5-methylindazole (3.13 g), paraformaldehyde (0.53 g) and pyrrolidine (2.1 g) were treated to obtain an oily product. The product was treated with ether-hydrochloric acid to produce 3.8 g of 1-pyrrolidinomethyl-3-phenyl-5-methylindazole hydrochloride having a melting point between 161°–162° C after recrystallization from ethanol-ether.

Analysis: Calcd. for $C_{19}H_{22}N_3Cl$: C, 69.61; H, 6.76; N, 12.82 (%) Found: C, 69.37; H, 6.69; N, 12.99 (%)

EXAMPLE 21 a. By the procedure similar to that described in Example 19, 3-phenylindazole (2.91 g), paraformaldehyde (0.50 g) and N-phenylpiperazine (4.87 g) were treated to obtain 4.3 g of 1-N-phenylpiperazinomethyl-3-phenylindazole having a melting point between 109°–110° C after recrystallization from ethanol.

Analysis: Calcd. for $C_{24}H_{24}N_4$: C, 78.23; H, 6.57; N, 15.21 (%) Found: C, 78.39; H, 6.42; N, 15.31 (%)

b. 3-Phenylindazole (9.71 g), paraformaldehyde (2.25 g) and 5% aqueous sodium hydroxide solution (1 ml) were added to ethanol (40 ml) and the mixture was heated under reflux for 3 hours. After cooling the reaction mixture, the precipitated crystals were recovered by filtration to obtain 8.7 g of 1-hydroxymethyl-3-phenylindazole having a melting point between 103°–105° C after recrystallization from ligroine.

Analysis: Calcd. for $C_{14}H_{12}N_2O$: C, 74.98; H, 5.39; N, 12.49 (%) Found: C, 74.92; H, 5.18; N, 12.61 (%)

1-Hydroxymethyl-3-phenylindazole obtained above and paraformaldehyde were treted by the procedure similar to that described in Example 19 to obtain the same product as produced in (a).

EXAMPLE 22 a. By the procedure similar to that described in Example 19, 3-phenyl-5-methylindazole (2.08 g), paraformaldehyde (0.35 g) and 2-(4′-chlorophenyl)-1,2,3,6-tetrahydro-4-methylpyridine (4.0 g) were treated to obtain 2.8 g of 1-[2′-(4′′′-chlorophenyl)-1′,-2′,3′,6′-tetrahydro-4′-methyl]-pyridinomethyl-3-phenyl-5-methylindazole (m.p. 130°–131° C).

Analysis: Calcd. for $C_{27}H_{26}N_3Cl$: C, 75.77; H, 6.12; N, 9.82 (%) Found: C, 76.19; H, 6.13; N, 10.28 (%)

b. By the procedure similar to that described in Example 19, 3-phenyl-5-methylindazole (13.7 g) and paraformaldehyde (2.4 g) were treated to obtain 13.1 g of 1-hydroxymethyl-3-phenyl-5-methylindazole (m.p. 109°–111° C).

Analysis: Calcd. for $C_{15}H_{14}N_2O$: C, 75.61; H, 5.92; N, 11.76 (%) Found: C, 75.54; H, 5.82; N, 11.76 (%)

1-Hydroxymethyl-3-phenylindazole obtained above and paraformaldehyde were treated by the procedure similar to that described in Example 19 to obtain the same product as produced in (a).

EXAMPLE 23

1-Hydroxymethyl-3-phenylindazole (2 g), morpholine (0.84 g) and 5% aqueous sodium hydroxide solution (1 ml) were dissolved in ethanol (30 ml), and the mixture was heated under reflux for 3 hours. After completion of the reaction, the mixture was concentrated under reduced pressure. The resulting oily residue was treated with ether-hydrochloric acid to obtain 1-morpholinomethyl-3-phenylindazole having a melting point between 166°–167° C (decomposition) after recrystallization from ethanol-ether.

Analysis: Calcd. for $C_{18}H_{20}N_3OCl$: C, 65.55; H, 6.11; N, 12.74 (%) Found: C, 65.48; H, 6.26; N, 12.58 (%)

EXAMPLE 24

3-Phenyl-5-methylindazole (4.17 g) was dissolved in dimethylformamide (70 ml) and to the solution was added sodium hydride 50% pure (0.96 g) followed by stirring at room temperature for 10 minutes. To the resulting mixture was added a solution of phthalimidopropyl chloride (4.47 g) in dimethylformamide (50 ml) followed by stirring at 95° C for 6 hours. The reaction mixture was poured into ice-water and then extracted with chloroform. The extract was washed with water, dried over sodium sulfate and concentrated under reduced pressure tp obtain 4.9 g of 1-phthalimidopropyl-3-phenyl-5-methylindazole having a melting point between 131°–132° C after recrystallization from methanol.

Analysis: Calcd. for $C_{25}H_{21}N_3O_2$: C, 75.93; H, 5.35; N, 10.63 (%) Found: C, 75.96; H, 5.27; N, 10.61 (%)

EXAMPLE 25

By the procedure similar to that described in Example 24, 3-phenyl-5-chloroindazole (9.2 g), sodium hydride 50% pure (2.3 g) and phthalimidopropyl chloride (9.0 g) were treated to obtain 10.4 g of 1-phthalimidopropyl-3-phenyl-5-chloroindazole. Recrystallization from methanol gave a product having a melting point between 121°–122° C.

Analysis: Calcd. for $C_{24}H_{18}N_3O_2Cl$: C, 69.31; H, 4.36; N, 10.10 (%) Found: C, 69.33; H, 4.43; N, 10.34 (%)

EXAMPLE 26

By the procedure similar to that described in Example 24, 3-phenylindazole (7.76 g), sodium hydride 50% pure (2.3 g) and phthalimidopropyl chloride (9.0 g) were treated to obtain 8.0 g of 1-phthalimidropropyl-3-phenylindazole having a melting point between 129°–130° C after recrystallization from methanol.

Analysis: Calcd. for $C_{24}H_{19}N_3O_2$: C, 75.57; H, 5.02; N, 11.02 (%) Found: C, 75.57; H, 4.99; N, 11.10 (%)

EXAMPLE 27

1-N-Monomethylcarbamoylethyl-3-phenylindazole (m.p. 111°–112° C) (50 g) was dissolved in anhydrous tetrahydrofuran (40 ml) and to the solution was added lithium aluminum hydride (1.5 g) under cooling with ice followed by heating under reflux for 20 min. while stirring. Aqueous ether and aqueous sodium hydroxide solution were added to the resulting reaction mixture to separate an organic layer. 10% Hydrochloric acid was added to the organic layer to separate water layer. The water layer was alkalized with the addition of an aqueous sodium hydroxide solution, extracted with benzene, and the extract was washed with water, dried over sodium sulfate and concentrated under reduced pressure to obtain 1.2 g of 1-N-monomethylaminopropyl-3-phenylindazole as an oily product. The product was converted to its oxalate by a conventional way and then recrystallized from methanol to obtain crystals having a melting point between 197°–198° C (decomposition).

Analysis: Calcd. for $C_{19}H_{21}N_3O_4$: C, 64.21; H, 5.91; N, 11.82 (%) Found: C, 64.26; H, 5.95; N, 11.97 (%)

EXAMPLE 28

By the procedure similar to that described in Example 27, 1-N-monomethylcarbamoylethyl-3-phenyl-5-chloroindazole (m.p. 123°–125° C) (5.0 g) was treated with the use of lithium aluminum hydride (1.5 g) to obtain 2.0 g of 1-N-monomethylaminopropyl-3-phenyl-5-chloroindazole oxalate having a melting point between 203°–204° C (decomposition) after recrystallization from ethanol.

Analysis: Calcd. for $C_{19}H_{20}N_3O_4Cl$: C, 58.54; H, 5.17; N, 10.78 (%) Found: C, 58.89; H, 5.16; N, 10.58 (%)

EXAMPLE 29

By the procedure similar to that described in Example 27, 1-N-monomethylcarbamoylethyl-3-phenyl-5-methylindazole (m.p. 128°–130° C) (5.0 g) was treated with the use of lithium aluminum hydride (1.5 g) to obtain 1.8 g of 1-N-monomethylaminopropyl-3-phenyl-5-methylindazole hydrochloride having a melting point between 148°–149° C after recrystallization from ethanol-ether.

Analysis: Calcd. for $C_{18}H_{22}N_3Cl$: C, 68.45; H, 7.02; N, 13.30 (%) Found: C, 68.70; H, 7.05; N, 13.35 (%)

EXAMPLE 30

Oily 1-N-phenylpiperazinocarbonylethyl-3-phenyl-5-methylindazole (4.0 g) which had been prepared by reacting in order 1-hydroxycarbonylethyl-3-phenyl-5-methylindazole with ethyl chlorocarbonate and N-phenyl-piperazine was treated with the use of lithium aluminum hydride (1.2 g) by the procedure similar to that described in Example 27 to obtain 6.1 g of 1-N-phenylpiperazino-propyl-3-phenyl-5-methylindazole hydrochloride having a melting point between 195°–200° C after recrystallization from ethanol-ether.

Analysis: Calcd. for $C_{27}H_{30}N_4 \cdot HCl$: C, 72.55; H, 6.99; N, 12.53 (%) Found: C, 72.46; H, 7.02; N, 12.57 (%)

EXAMPLE 31

By the procedure similar to that described in Example 27, 1-N,N-dimethylcarbamoylethyl-3-phenyl-5-methylindazole (m.p. 99°–100° C) (5.0 g) was treated with the use of lithium aluminum hydride (1.5 g) to obtain 1.9 g of 1-N,N-dimethylaminopropyl-3-phenyl-5-methyl-indazole oxalate having a melting point between 184°–185° C after recrystallization from ethanol.

Analysis: Calcd. for $C_{21}H_{25}N_3O_4$: C, 65.78; H, 6.57; N, 10.96 (%) Found: C, 65.70; H, 6.61; N, 10.82 (%)

EXAMPLE 32

By the procedure similar to that described in Example 27, 1-carbamoylethyl-3-phenyl-5-chloroindazole (m.p. 156°–157° C) (5.0 g) was treated with the use of lithium aluminum hydride (1.5 g) to obtain 2.0 g of 1-aminopropyl-3-phenyl-5-chloroindazole hydrochloride having a melting point between 163°–164° C after recrystallization from ethanol-ether.

Analysis: Calcd. for $C_{16}H_{17}N_3Cl_2$: C, 59.64; H, 5.32; N, 13.04 (%) Found: C, 59.65; H, 5.42; N, 13.20 (%)

EXAMPLE 33

1-Phthalimidopropyl-3-phenyl-5-chloroindazole (8.3 g) and hydrazine hydrate (2.0 g) were added to ethanol (150 ml) followed by heating under reflux for 3 hours. The reaction mixture was concentrated under reduced pressure and to the residue were added benzene (150 ml) and 10% aqueous sodium hydroxide solution (200 ml) followed by stirring at room temperature for 1 hour. The organic layer was separated from the mixture and it was washed with water, dried over sodium sulfate and concentrated under reduced pressure to obtain 5.5 g of 1-aminopropyl-3-phenyl-5-chloroindazole as an oily product. The product was treated with ether-hydrochloric acid to form its hydrochloride. After recrystallization from ethanol-ether, the product had a melting point between 163°–164° C.

Analysis: Calcd. for $C_{16}H_{17}N_3Cl_2$: C, 59.64; H, 5.32; N, 13.04 (%) Found: C, 59.75; H, 5.28; N, 13.19 (%)

EXAMPLE 34

By the procedure similar to that described in Example 33, 1-phthalimidopropyl-3-phenyl-5-methylindazole (5.0 g) and hydrazine hydrate (1.5 g) were treated to obtain 3.1 g of 1-aminopropyl-3-phenyl-5-methylindazole as an oily product. The product was converted by a conventional way to its hydrochloride having a melting point between 161°–163° C.

Analysis: Calcd. for $C_{17}H_{20}N_3Cl$: C, 67.65; H, 6.68; N, 13.92 (%) Found: C, 67.64; H, 6.76; N, 13.63 (%)

EXAMPLE 35

By the procedure similar to that described in Example 33, 1-phthalimidopropyl-3-phenylindazole (6.0 g) and hydrazine hydrate (2.0 g) were treated to obtain 3.8 g of 1-aminopropyl-3-phenylindazole as an oily product.

Infrared Absorption Spectra: (neat) $(cm^{-1})$
3370, 3050, 2930, 2870,
1615, 1605, 1495, 1150,
778, 750, 695
NMR: $\delta(CDCl_3)$
1.57 (—NH$_2$, 2H)
2.06 (—C—CH$_2$—C—, 2H, quintlet)
2.73 (—CH$_2$NH$_2$, 2H, triplet)

4.52 (N\\_/ , 2H, triplet)
  |
  CH$_2$—CH$_2$—
7.0–8.1 (aromatic proton, 9H)

EXAMPLE 36

3-Phenyl-5-fluoroindazole (2.12 g), paraformaldehyde (0.33 g), piperidine (1 g) and 1N aqueous sodium hydroxide solution (1 ml) were added to ethanol (30 ml) followed by heating under reflux for 3 hours. The reaction mixture was concentrated under reduced pressure and the residue was dissolved in benzene, washed with water, dried over sodium sulfate and concentrated under reduced pressure to obtain 1.9 g of 1-piperidinomethyl-3-phenyl-5-fluoroindazole having a melting point between 82°–84° C after recrystallization from methanol.

Analysis: Calcd. for $C_{19}H_{20}N_3F$: C, 73.76; H, 6.52; N, 13.58 (%) Found: C, 73.94; H, 6.46; N, 13.83 (%)

EXAMPLE 37

3-Phenyl-5-chloroindazole (4.57 g), piperidinoethyl chloride (3.6 g), and triethylbenzylammonium chloride (0.5 g) were added to 50% aqueous sodium hydroxide solution (5 ml) followed by stirring at 70° C for 1 hour. After completion of the reaction, the mixture was extracted with benzene and the extract was washed with water, dried over sodium sulfate and concentrated. The residue was treated with ethanol-hydrochloric acid to obtain 4.3 g of 1-piperidinoethyl-3-phenyl-5-chloroindazole hydrochloride having a melting point between 230°–235° C after recrystallization from acetone.

Analysis: Calcd. for $C_{20}H_{23}N_3Cl_2$: C, 63.83; H, 6.16; N, 11.17 (%) Found: C, 64.26; H, 6.19; N, 11.34 (%)

EXAMPLE 38

By the procedure similar to that described in Example 27, 1-N-mono(n-butyl)carbamoylethyl-3-phenylindazole (3.5 g) was treated with the use of lithium aluminum hydride (1.0 g) to obtain 0.3 g of 1-n-butylaminopropyl-3-phenylindazole as an oily product. The product was converted to its oxalate which had a melting point of 181°–183° C after recrystallization from methanol.

Analysis: Calcd. for $C_{22}H_{27}N_3O_4$: C, 66.48; H, 6.85; N, 10.57 (%) Found: C, 66.31; H, 6.90; N, 11.66 (%)

EXAMPLE 39

By the procedure similar to that described in Example 27, 1-N-monoallylcarbamoylethyl-3-phenylindazole (3.5 g) was treated with the use of lithium aluminum hydrie (1.0 g) to obtain 0.9 g of 1-monoallylaminopropyl-3-phenylindazole as an oily product. The product was converted to its oxalate which had a melting point of 203° C after recrystallization from methanol.

Analysis: Calcd. for $C_{21}H_{23}N_3O_4$: C, 66.13; H, 6.08; N, 11.02 (%) Found: C, 66.19; H, 6.08; N, 11.12 (%)

What is claimed is:

1. Indazole derivatives represented by the formula

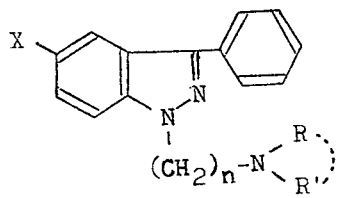

wherein X is hydrogen, halogen atom or lower alkyl group; R and R' each is hydrogen, lower alkyl group of lower alkenyl group; R and R' when taken together with the nitrogen atom to which they are attached, is piperidino, morpholino, N-methyl-piperazino, N-phenylpiperazino, pyrrolidino, 2-(4'-chlorophenyl)-1,2,3,6-tetrahydro-4-methylpyridino, or phthalimido group; and n is an integer of 2 or 3.

2. 1-Dimethylaminoethyl-3-phenylindazole in accordance with claim 1.

3. 1-Dimethylaminoethyl-3-phenyl-5-chloroindazole in accordance with claim 1.

4. 1-Dimethylaminoethyl-3-phenyl-5-methylindazole in accordance with claim 1.

5. 1-Diethylaminoethyl-3-phenyl-5-chloroindazole in accordance with claim 1.

6. 1-Diethylaminoethyl-3-phenyl-5-methylindazole in accordance with claim 1.

7. 1-Diethylaminoethyl-3-phenylindazole in accordance with claim 1.

8. 1-Dimethylaminopropyl-3-phenylindazole in accordance with claim 1.

9. 1-Dimethylaminopropyl-3-phenyl-5-chloroindazole in accordance with claim 1.

10. 1-Dimethylaminopropyl-3-phenyl-5-bromoindazole in accordance with claim 1.

11. 1-Dimethylaminopropyl-3-phenyl-5-methylindazole in accordance with claim 1.

12. 1-Piperidinopropyl-3-phenylindazole in accordance with claim 1.

13. 1-Piperidinopropyl-3-phenyl-5-methylindazole in accordance with claim 1.

14. 1-Diethylaminopropyl-3-phenyl-5-methylindazole in accordance with claim 1.

15. 1-Morpholinopropyl-3-phenyl-5-chloroindazole in accordance with claim 1.

16. 1-Morpholinopropyl-3-phenyl-5-methylindazole in accordance with claim 1.

17. 1-N-methylpiperazinopropyl-3-phenylindazole in accordance with claim 1.

18. 1-N-methylpiperazinopropyl-3-phenyl-5-methylindazole in accordance with claim 1.

19. 1-Diallylaminopropyl-3-phenyl-5-methylindazole in accordance with claim 1.

20. 1-N-phenylpiperazinomethyl-3-phenylindazole.

21. 1-[2'-(4''-chlorophenyl)-1',2',3',6'-tetrahydro-4'-methyl]-pyridinomethyl-3-phenyl-5-methylindazole.

22. 1-Phthalimidopropyl-3-phenyl-5-methylindazole in accordance with claim 1.

23. 1-Phthalimidopropyl-3-phenyl-5-chloroindazole in accordance with claim 1.

24. 1-Phthalimidopropyl-3-phenylindazole in accordance with claim 1.

25. 1-N-monomethylaminopropyl-3-phenylindazole in accordance with claim 1.

26. 1-N-monomethylaminopropyl-3-phenyl-5-chloroindazole in accordance with claim 1.

27. 1-N-monomethylaminopropyl-3-phenyl-5-methylindazole in accordance with claim 1.

28. 1-N-phenylpiperazinopropyl-3-phenyl-5-methylindazole in accordance with claim 1.

29. 1-Aminopropyl-3-phenyl-5-chloroindazole in accordance with claim 1.

30. 1-Aminopropyl-3-phenyl-5-methylindazole in accordance with claim 1.

31. 1-Aminopropyl-3-phenylindazole in accordance with claim 1.

32. 1-Piperidinoethyl-3-phenyl-5-chloroindazole in accordance with claim 1.

33. 1-Mono-n-butylaminopropyl-3-phenylindazole in accordance with claim 1.

34. 1-Monoallylaminopropyl-3-phenylindazole in accordance with claim 1.

* * * * *

UNITED STATES PATENT AND TRADEMARK OFFICE
CERTIFICATE OF CORRECTION

PATENT NO. : 3,994,890
DATED : November 30, 1976
INVENTOR(S) : Yasuo Fujimura et al.

It is certified that error appears in the above-identified patent and that said Letters Patent are hereby corrected as shown below:

[57] Abstract, formula [I] should appear as follows:

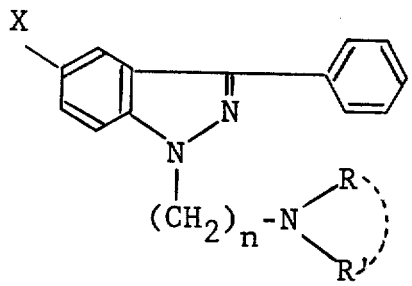

Column 1, line 30, formula [II] should appear as follows:

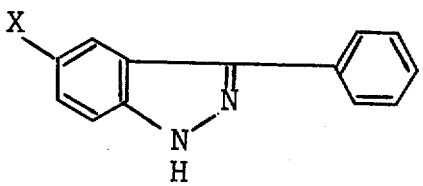

UNITED STATES PATENT OFFICE

CERTIFICATE OF CORRECTION

Patent No. 3,994,890  Dated November 30, 1976

Inventor(s) Yasuo Fujimura et al

It is certified that error appears in the above-identified patent and that said Letters Patent are hereby corrected as shown below:

Column 3, line 53, "bydroxide" should read --hydroxide--

Column 5, Table 3, "mouse 580 660" should read --mouse ♂ 580 ♀ 660--

Signed and Sealed this

Tenth Day of May 1977

[SEAL]

Attest:

RUTH C. MASON
Attesting Officer

C. MARSHALL DANN
Commissioner of Patents and Trademarks